United States Patent
Cobb

(10) Patent No.: US 9,604,216 B2
(45) Date of Patent: Mar. 28, 2017

(54) SAMPLE PREPARATION PAPER CARTRIDGE

(71) Applicant: Epistem Limited, Manchester (GB)

(72) Inventor: Benjamin Cobb, North Wraxall (GB)

(73) Assignee: Epistem Limited, Manchester (GB)

( * ) Notice: Subject to any disclaimer, the term of this patent is extended or adjusted under 35 U.S.C. 154(b) by 0 days.

(21) Appl. No.: 14/767,265

(22) PCT Filed: Feb. 11, 2014

(86) PCT No.: PCT/GB2014/050391
§ 371 (c)(1),
(2) Date: Aug. 11, 2015

(87) PCT Pub. No.: WO2014/122486
PCT Pub. Date: Aug. 14, 2014

(65) Prior Publication Data
US 2016/0030939 A1    Feb. 4, 2016

(30) Foreign Application Priority Data
Feb. 11, 2013 (GB) .................................. 1302346.0

(51) Int. Cl.
*B01L 3/00* (2006.01)
*C12N 15/10* (2006.01)
*G01N 1/28* (2006.01)

(52) U.S. Cl.
CPC ............... *B01L 3/52* (2013.01); *B01L 3/5023* (2013.01); *C12N 15/1003* (2013.01);
(Continued)

(58) Field of Classification Search
CPC ........................ B01L 2300/0816; B01L 3/5023
(Continued)

(56) References Cited

U.S. PATENT DOCUMENTS

| 4,549,655 A | 10/1985 | Forsythe, Jr. et al. |
| 6,184,040 B1 | 2/2001 | Polizzotto et al. |

(Continued)

FOREIGN PATENT DOCUMENTS

| WO | WO-91/01179 A1 | 2/1991 |
| WO | WO-2012/103511 A2 | 8/2012 |

OTHER PUBLICATIONS

International Search Report for PCT/GB2014/050391, 3 pages (Jun. 6, 2014).
Written Opinion PCT/GB2014/050391, 5 pages (Jun. 6, 2014).

*Primary Examiner* — Natalia Levkovich
(74) *Attorney, Agent, or Firm* — Choate, Hall & Stewart LLP; Brenda Herschbach Jarrell; Michael L. Vetter

(57) ABSTRACT

A sample preparation cartridge is described having a lower portion having four integrally-formed leaf springs, and a raised lower base part which is slightly below the level of the leaf springs. An upper portion of the cartridge engages with the lower portion, via four paired pins and holes formed in the lower and upper portions. The upper portion includes three well-shaped openings formed in the central region of the upper portion. Between the upper and lower portions is placed a sheet of sample preparation paper, resting on the leaf springs, which raise the lower face of the paper away from the raised lower base part, leaving a small air gap between the base and the paper. The upper face of the paper is in contact with the well-shaped openings of the upper portion. The user loads a liquid sample into the openings, and the paper wicks the liquid sample away from the loading location, leaving cellular debris in the place of application. Applying pressure to the upper portion of the cartridge urges the paper into contact with the raised base portion, so (Continued)

providing a firm base which allows the user to remove sections of the paper, using for example a biopsy needle, for further processing.

25 Claims, 3 Drawing Sheets

(52) U.S. Cl.
CPC ... *B01L 2200/025* (2013.01); *B01L 2300/021* (2013.01); *B01L 2300/022* (2013.01); *B01L 2300/0654* (2013.01); *B01L 2300/0681* (2013.01); *B01L 2300/0825* (2013.01); *B01L 2300/126* (2013.01); *B01L 2300/16* (2013.01); *B01L 2300/165* (2013.01); *B01L 2400/0406* (2013.01); *B01L 2400/0633* (2013.01); *G01N 1/28* (2013.01)

(58) Field of Classification Search
USPC .................................................. 422/554, 430
See application file for complete search history.

(56) References Cited

U.S. PATENT DOCUMENTS

| | | | |
|---|---|---|---|
| 6,867,051 B1 * | 3/2005 | Anderson | ............ G01N 21/474 250/461.2 |
| 2012/0104096 A1 | 5/2012 | Lee et al. | |

\* cited by examiner

SAMPLE PREPARATION PAPER CARTRIDGE

FIELD OF THE INVENTION

The present invention relates to a cartridge for sample preparation paper, to be used, for example, when preparing samples for molecular biology processing techniques such as nucleic acid amplification and/or detection.

BACKGROUND TO THE INVENTION

PCR is a convenient method for amplifying particular target nucleic acid sequences in a biological sample. It is often used for forensics or diagnostics purposes, in order to detect markers which may be used for example to identify an individual to whom a DNA sample belongs; or to determine whether a particular pathogen is present in a sample. For such purposes, it is useful to have a relatively rapid assay, which may mean that extensive sample preparation and clean up cannot be undertaken.

Most clinical samples require some processing to make the sample compatible with PCR. It is known to use paper-type filters to remove inhibitors and to provide clean sample for the PCR reaction.

It is among the objects of the present invention to provide a convenient means for sample preparation for samples for biological analysis, in particular making use of paper-type filters. This is achieved, in part, by the provision of housing within which the sample preparation paper may be placed for sample preparation.

SUMMARY OF THE INVENTION

According to a first aspect of the present invention, there is provided a sample preparation cartridge comprising:
a lower portion having a base,
an upper portion engageable with and removable from the lower portion, and comprising at least one well shaped opening; and
at least one sprung member located between the lower and upper portions when the upper portion is engaged with the lower portion;
the cartridge being configured such that a sample preparation paper may be received between the upper and lower portions located adjacent the well shaped opening, and that the paper rests on the at least one sprung member so as to separate the paper from the base of the lower portion; and
wherein applying pressure to the upper portion causes the at least one sprung member to compress, and thereby urges the paper into contact with at least a portion of the base.

This arrangement has a number of advantages for sample processing. In particular, the well shaped opening will serve to channel liquid samples to the sample paper, thereby guiding and concentrating the sample to a small "spot" on the paper. The initial configuration of the cartridge, where the paper is separated from the base of the lower portion, allows air to circulate beneath the paper, thereby aiding sample wicking into the paper and drying. The compressed configuration, where the sample paper is in contact with the base, allows the user to easily cut portions of the sample paper using, for example, a biopsy punch, for further processing and analysis without having to disassemble the cartridge and remove the complete paper.

Preferably the base includes a raised portion configured to align with the well shaped opening, and to contact the paper when the sprung member is compressed.

The sprung member is preferably an element of the lower portion, although in certain embodiments, the spring member may be separate from both the lower portion and the upper portion. Preferably the cartridge comprises two, more preferably four sprung members. The sprung members may be leaf springs. The sprung members are preferably formed integrally with the lower portion; for example, the whole may be formed from a single piece of molded plastic material.

Preferably the upper portion comprises a plurality of well shaped openings; in preferred embodiments, there are three such openings.

The upper portion may be made from a plastics material. Preferably, the upper portion is translucent and/or clear. This allows visual confirmation as to whether sample paper is present in the cartridge. Preferably the plastics material is hydrophobic; for example, it may be polycarbonate, such as Makrolon®. This helps to repel fluid samples and guide them into the wells so as to contact the sample paper. The plastics material may be functionalised. For example, the material may be modified with groups to assist in lysis of cellular material in samples. In a preferred embodiment, the material is functionalised with one or more biocidal agents, preferably SiQACs, as described below in connection with derivatised sample papers.

In certain embodiments of the invention, the cartridge may further comprise a sample paper located between the upper and lower portions. The paper is preferably a cellulose material; for example, a cellulose filter paper or a cellulose matrix. The cellulose material may be a composite paper; for example, a composite cellulose paper may comprise a lateral flow layer, to remove liquid and low molecular weight contaminants and inhibitors from the sample which is deposited on a surface of the paper. Cellulose has the advantage that it has a number of exposed hydroxyl groups to which biocidal agents may be attached. In preferred embodiments, the sample paper is functionalised with one or more biocidal agents capable of i) weakening cell membrane, cell wall, viral envelope, or viral capsid of biological material in a sample; or ii) lysing cellular or viral material in a sample.

The biocidal agent preferably comprises multiple functional groups. The functional groups preferably include a binding moiety, which is involved in binding the agent to the substrate; a hydrophobic moiety; and a charged moiety. The hydrophobic moiety is able to interact with and penetrate the cell wall or cell membrane. In preferred embodiments, the hydrophobic moiety may be an alkyl chain, for example C5-C30 alkyl, preferably C10-C20 alkyl. As the alkyl chain penetrates the delicate cell wall, the wall is weakened and punctured. The charged moiety is preferably positively charged, and is able to attract a charged cell wall, and can disrupt ion flow and homeostasis on contacting a cell membrane, thereby helping to disrupt the cell and release the nucleic acids. The charged moiety is preferably a quaternary ammonium group. The binding moiety may comprise a hydroxyl group.

In preferred embodiments, the functional groups are preferably an alkyl chain (the hydrophobic moiety), a silyl group (the binding moiety), and an ammonium chloride group (the charged moiety).

Preferred biocidal agents include silylated quaternary ammonium compounds (SiQACs); in particular 3-(trimethoxysilyl)propyldimethyloctadecyl ammonium chloride (3-TPAC). Other biocidal agents include benzyl ammonium chlorides. The lethal mode of action of SiQACs is generally accepted to proceed by adsorption of the positively charged molecule onto the negatively charged cell surface, disruption of the cell membrane by a lipophilic chain on the SiQAC molecule, and diffusion through the membrane leading to cell lysis.

The skilled person will be aware of other suitable biocidal agents which may be used. The selection of a particular agent will be guided by the presence of the preferred functional groups described above, and the nature of the intended biological sample—for example, where the sample to be processed is a mammalian cellular sample, then there is no cell wall to penetrate, and other functional groups may be appropriate.

Examples of other biocidal agents which may be used in the present invention include:
 a) telechelic poly(2-alkyl-1,3-oxazolines);
 b) cellulose with an antimicrobial DDA group grafted via PEtOx, which kills approaching microbial cells on contact (Bieser et al (2011), Contact-Active Antimicrobial and Potentially Self-Polishing Coatings Based on Cellulose. Macromol. Biosci., 11, 111-121);
 c) saponins are steroid or triterpenoid glycosides, common in a large number of plants, and have long been known to have a lytic action on erythrocyte membrane and many saponins are known to be antimicrobial (Francis et al, British Journal of Nutrition (2002), 88, 587-605). Extensive research has been carried out into the membrane-permeabilising properties of saponins. These structurally diverse compounds have also been observed to kill protozoans and to act as anti-fungal and antiviral agents. Isolated cell membranes from human erythrocytes when treated with saponin developed pores of 40-50 A° diameter as against the 80 A° pores produced in artificial membranes (Seeman et al. 1973 Structure of membrane holes in osmotic and saponin hemolysis. Journal of Cell Biology 56, 519-527).

For a review of other Antimicrobial Polymers in Solution and on Surfaces see Siedenbiedel and Tiller (2012) Polymers, 4, 46-71.

As noted above, the upper portion of the cartridge may likewise include one or more biocidal agents. These may be the same as or different to biocidal agents present in the sample paper. In preferred embodiments, both cartridge and paper are functionalised with SiQACs.

The sample paper may comprise a colour change reagent, to indicate when and/or where sample has been applied to the paper. For example, the reagent may change colour when wet, and/or after drying. The sample paper may include indicia to mark where sample is to be applied; for example, printed markings.

In certain embodiments, the sample paper may further comprise one or more reagents for conducting a desired reaction; for example, the paper may comprise lyophilised PCR reagents, and/or lyophilised enzymes. These reagents will then be reconstituted when the sample paper is contacted with liquid in a reaction vessel. In this way the reagents may be kept separate from one another until ready to be activated to carry out a reaction. The paper may comprise multiple reagents; these may be combined within the paper, or may be kept separate, for example being incorporated into separate layers of a composite paper. The reagents may be incorporated into an additional layer of a composite paper.

In certain embodiments, the paper may be Whatman FTA® card, available from Whatman Ltd, for example an FTA Classic Card, catalogue number WB120305. FTA cards contain chemicals that lyse cells, denature proteins and protect nucleic acids from nucleases, oxidative, and UV damage.

The sample paper may be a composite paper. In preferred embodiments, the composite paper includes an adsorbent upper layer, and a lateral flow layer. The paper may also include a semipermeable layer disposed between the upper layer and the lateral flow layer.

In preferred embodiments, the absorbent upper layer has a number of optimal characteristics. The material should be hydrophilic and should not bind irreversibly nucleic acids. The absorbent material must not release PCR inhibitors and/or release substances or chelating reagents used for the whitening process that may interfere with PCR. The absorbent material is preferably made of cellulose (although porous polymers such as polyesters may also be equally effective). Important characteristics are Liquid Filtration Speed and Density, Basis Weight and Water Absorbency. For example, preferred materials include Shleicher & Schuell Inc. 903. Alternatives are; Schelicher & Schuell "GB002", "GB003" and "GB004", Fairfield, N.J. "BFC1" and Whatmann "3MM" (although this last one would require impregnation with a surfactant mixture).

Preferred values for the important characteristics include:

| Liquid filtration speed | Densometer | Retained precipitates |
|---|---|---|
| TAPPI T471 | TAPPI T471 | ASTM D981-56 |
| u.m. 572 | u.m. 572 | (8 to 30 um particles) |
| ASTM E832-9.3 | ASTM 726 | |
| (7.3 seconds) | (20 seconds) | |
| Surface | Basis weight | Caliper |
| Smooth, not hardened | TAPPI T471 | TAPPI T471 |
| | u.m. 572 | u.m. 572 |
| | TAPPI T410 | TAPPI T411 |
| | ASTM 646 | ASTM 643 |
| | (179 g/m2) | (0.52 mm thick) |
| Water absorbency | Klemm | Wet strength - 5 sheets |
| TAPPI T441 | TAPPI T441 | TAPPI T471 |
| ASTM 3285 | ASTM 3285 | ASTM 774 |
| (4.5 g/100 cc) | (34/16 deg/min) | (7.0 psi) |

The preferred upper layer may have any or all of these values, alone or in any combination.

The lateral flow layer may be nitrocellulose.

The adsorbent layer is preferably 0.5-1 mm in thickness; the lateral flow layer may be 0.1-0.2 mm in thickness.

The sample paper may further comprise a support layer; for example, a plastics support, such as polyester, disposed adjacent the lateral flow layer. This may be of the same or similar order of thickness as the lateral flow layer; for example, around 0.1 mm.

The paper properties allow the paper to rapidly wick the liquid into the paper, leaving target organisms on the surface, and dehydrate the cellular material on the surface weakening the cell walls and making them lysable by heat. The paper also locks/removes inhibitors in the paper.

These and other desirable features of suitable papers can be found in our co-pending patent applications PCT/GB2012/052847 (describing the composite paper), and GB 1209229.2 (describing the functionalised biocidal paper). The contents of both these applications are incorporated herein by reference, and the reader is referred to these for further details of suitable papers.

In a further aspect of the present invention, there is provided a kit comprising:
 a) a sample preparation cartridge comprising:
 a lower portion having a base;

an upper portion engageable with and removable from the lower portion, and comprising at least one well shaped opening; and at least one sprung member located between the lower and upper portions when the upper portion is engaged with the lower portion;

the cartridge being configured such that a sample preparation paper may be received between the upper and lower portions located adjacent the well shaped opening, and that the paper rests on the at least one sprung member so as to separate the paper from the base of the lower portion;

wherein applying pressure to the upper portion causes the at least one sprung member to compress, and thereby urges the paper into contact with at least a portion of the base; and b) a sample preparation paper.

Further features of the cartridge and the paper may be as described above.

BRIEF SUMMARY OF THE DRAWINGS

These and other aspects of the invention will be described with reference to the accompanying drawings, in which.

DETAILED DESCRIPTION OF THE INVENTION

Figure 1:
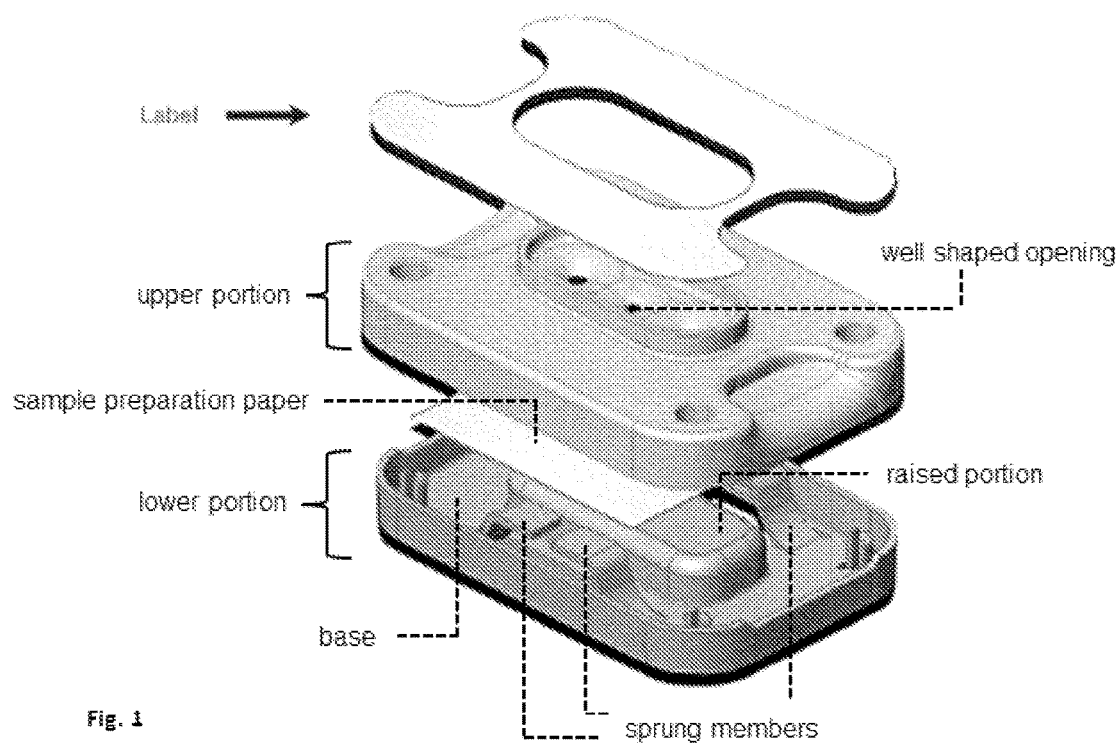
FIG. 1 shows an exploded view of a cartridge in accordance with an embodiment of the invention.

An exploded view of a cartridge in accordance with an embodiment of the invention is shown in FIG. 1. The cartridge includes a lower portion having four integrally-formed leaf springs, and a raised lower base part which is slightly below the level of the leaf springs. An upper portion of the cartridge engages with the lower portion, via four paired pins and holes formed in the lower and upper portions. The upper portion includes three well-shaped openings formed in the central region of the upper portion.

Between the upper and lower portions is placed a sheet of sample preparation paper. This paper rests on the leaf springs, which raise the lower face of the paper away from the raised lower base part, leaving a small air gap between the base and the paper. The upper face of the paper is in contact with the well-shaped openings of the upper portion.

The upper portion is formed of a hydrophobic plastic material, such as polycarbonate (for example, Makrolon®). This may be derivatised, as described below.

In use, once the cartridge is assembled, the user may load a liquid sample (for example, containing cellular material) into the well-shaped openings. These openings serve to channel and concentrate the sample to the adjacent locations on the sample paper. The hydrophobic nature of the upper portion reduces the amount of sample fluid remaining on the cartridge, channeling it into the wells instead. The paper wicks the liquid sample away from the loading location, leaving cellular debris in the place of application. Both the paper and the well-shaped openings may be functionalised with active groups intended to promote cellular lysis, as described below, in order to release nucleic acids or other cell contents into the paper. Since the paper is raised from the base portion, allowing air to circulate beneath the paper, this aids in drying of the sample on the paper.

The user then applies pressure to the upper portion of the cartridge, thereby pushing against the paper and compressing the leaf springs. This urges the paper into contact with the raised base portion, so providing a firm base which allows the user to remove sections of the paper, using for example a biopsy needle, for further processing.

The cartridge may then be disposed of, or the used paper removed and the cartridge washed ready for further use.

The cartridge may also include a label which may identify the particular cartridge, for sample tracking and monitoring, or which may allow the user to make notes of the nature of the sample loaded. The label may include a machine-readable tag, for example, a bar code or an RFID tag. This may allow samples to be tracked, and details of the samples easily archived if desired.

As noted above, the paper and/or the upper portion of the cartridge may be functionalised to include biocidal agents which assist in lysis of cellular material. A preferred functional group is a SiQAC moiety.

Figure 2:
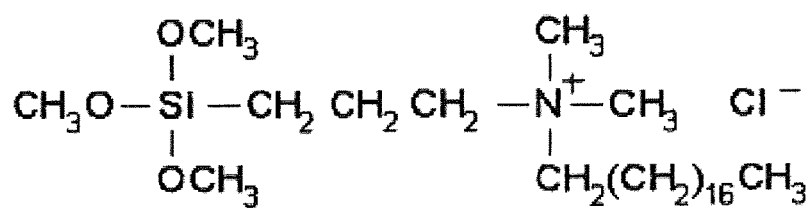
FIG. 2 shows the structure of a SiQAC molecule.

The structure of a SiQAC molecule [3-(trimethoxysilyl) propyldimethyloctadecyl ammonium chloride (3-TPAC)] is shown in FIG. 2. 3-TPAC was first described in 1972 (http://www.ncbi.nlm.nih.gov/pmc/articles/PMC380687/pdf/applmicro00052-0033.pdf).

There are many versions of the basic chemistry (e.g. benzyl ammonium chlorides BAC), but all share similar key ingredients: ammonium chloride variant (the active antimicrobial), silicon as a binding agent (the silyl part) and an alkane chain. The ammonium chloride is a quaternary ammonium group which is attached to two methyl groups and effectively two longer chain alkyl groups. This cationic function confers anti-microbial properties which result in the breaking of bacterial, fungal and viral membranes, releasing the nucleic acid content. The hydrophobic alkane chain penetrates cell walls. The trimethoxysilyl group binds the molecule to a substrate (e.g. cellulose) via the active hydroxyl group.

Quaternary ammonium compounds are lethal to a wide variety of organisms including bacteria, fungi and coated viruses, and to a lesser extent to endospores, *Mycobacterium tuberculosis* and non-enveloped viruses. Many biocidal polymers are known with quaternary ammonium groups. Quaternary ammonium (QA) compounds are among the most widely used antibacterial agents for medical and public health applications, and have been shown to be effective against both gram negative and gram positive bacteria (Tashiro (2001) Macromol. Mater. Eng.; 286, 63-87).

Cationic polymers with QA groups generally exhibit higher antimicrobial activities than their corresponding low molecular weight monomers (Ikeda and Tazuke, 1983, Makromol. Chem., Rapid Commun. 4 (1983) 459-461). The higher activity is attributed to greater electrostatic attraction between the cell and polymer due to the greater charge density of the polymer.

SiQACs work through a two-step process. The positively charged action on the SiQAC molecule attracts the negatively charged cell wall of the microorganism. Initially, the hydrophobic alkyl chain penetrates the similarly hydrophobic cell wall of an organism that it comes in contact with. As the alkyl chain penetrates the delicate cell wall, the wall is weakened and punctured. Second, as the cationic quaternary ammonium group comes in contact with the cell wall it disrupts the ion flow and causes leakage into or out of the cell wall, usually resulting in the cell losing its contents or bursting depending on the ionic environment. The charged quaternary ammonium alkyl group remains unchanged and is available to repeat the process indefinitely.

Because of this "physical" and "electrical" killing mechanism, microbes do not get an opportunity to develop resistance or immunity to the SiQAC.

Quaternary ammonium compounds are widely used as disinfectants, antiseptics, pharmaceutical products, and cosmetics and could be an alternative in fruit and vegetables disinfection. All quaternary ammonium compounds (QACs) are cationic compounds that possess a basic structure (NH4+). These compounds penetrate into the bacterial cell wall, reacting with the cytoplasmic membrane inducing wall lysis caused by autolytic enzymes (McDonnell, G. & Russell, A. D. 1999 Antiseptics and disinfectants: activity, action and resistance. Clinical Microbiology Reviews 12, 147-179).

The trimethoxysilyl groups react with hydroxyl groups on surfaces such as glass and cotton to form covalent bonds that retain the QA compound at the surface and prevent it from dissolving in water. The trimethoxysilyl groups can also react with each other to form a highly stable cross-linked silane coating bound to treated surfaces. These coatings have been shown to impart biocidal activity to surfaces in many applications without the release of chemical agents into the surrounding environment (Isquith et al, 1972 Appl. Microbiol. 24, 859; Isquith et al, 1973 U.S. Pat. No. 3,730,701; Speier and Malek, 1982 J of Colloid and Interface Science 89, 68; Walters et al., 1973, J., Appl. Microbiol. 25, 253).

While these coatings were very effective as a fungicide and an antibacterial agent, they have been ineffective against spores.

Figure 3:
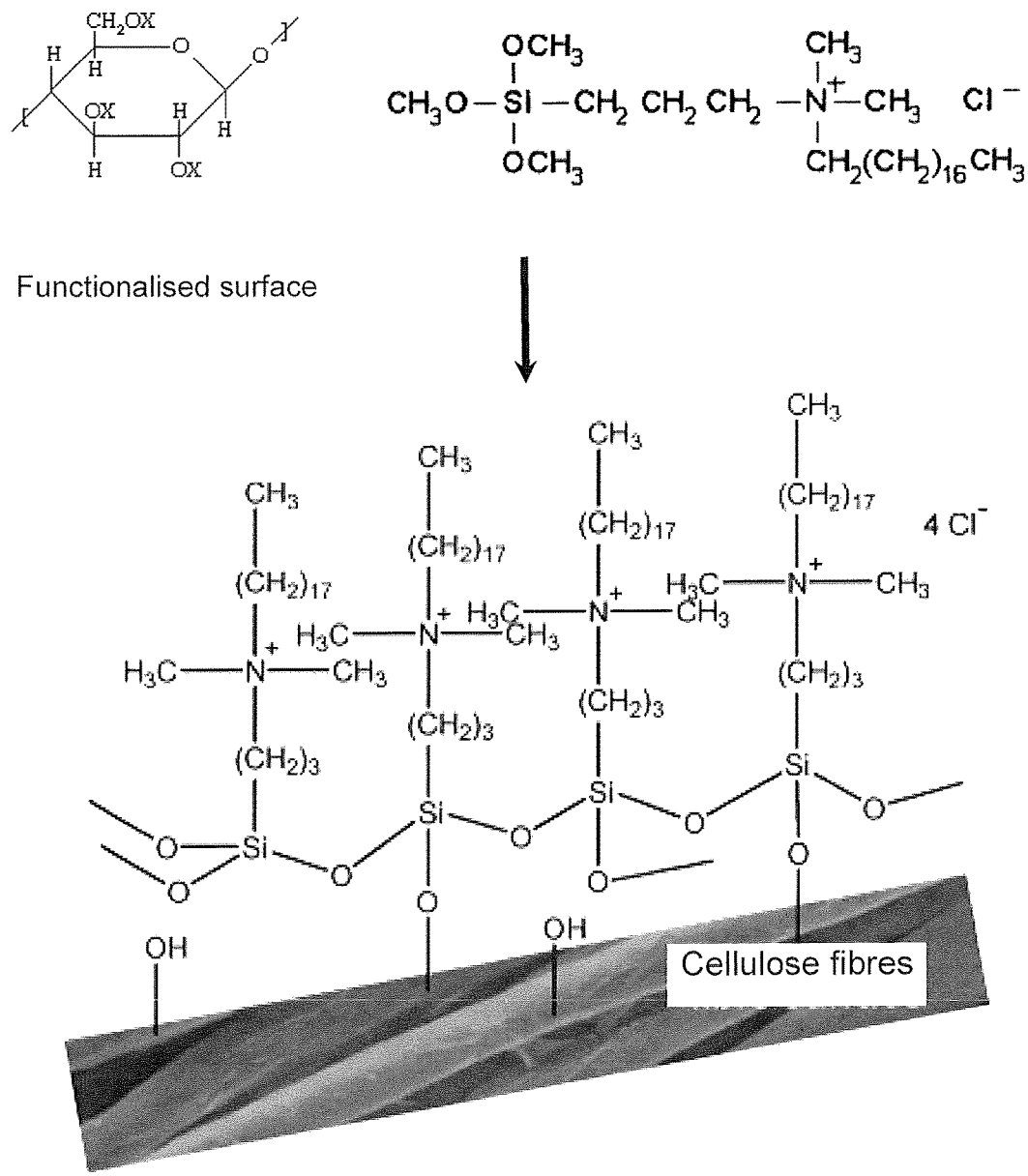
FIG. 3 illustrates the functionalisation of cellulose with a SiQAC molecule, 3-TPAC.

FIG. 3 illustrates the functionalisation of cellulose with a SiQAC molecule, 3-TPAC. In unaltered native cellulose, X represents hydrogen, forming a number of pendant hydroxyl (OH) groups. In the faster initial stage a bond forms between the molecule and the hydroxyl group forming a silyl ether. In the second slower step cross-links are formed between adjacent dimethoxysilyl groups to form a random silicone ether polymer aligned parallel to the substrate surface.

The cationic moiety plays no part in the surface binding but is available yet bound to the substrate surface. Its structure is analogous to the quaternary ammonium compounds recognised as topical antiseptics of which didecyldimethylammonium chloride (DDAC) is a typical example.

The mechanism whereby the SiQAC molecule becomes bound to the substrate surface is similar chemically to that in the cross-linking of polyethene to form PEX.

EXAMPLE

Paper Functionalisation

Three alternative paper functionalisation methods are given:

Process A

Figure 4:
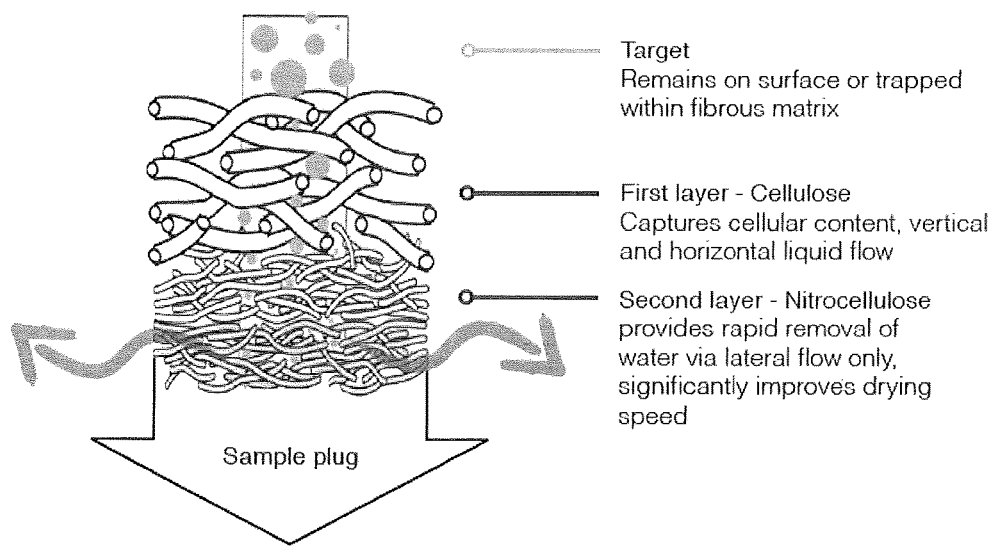
FIG. 4 illustrates a sample preparation paper which may be used with the cartridge.

Paper functionalised with 20 µl SiQAC (3-TPAC) solution, dried for 24 hours and then washed in 20 µl 5 mM TRIS-Cl [pH 9.0], 0.2 mM MgCl2 then dried and either;
  i. Apply the sample, dry for 20', remove disc and add 20 µl of miliQ water for PCR, or
  ii. Apply the sample, dry for 20', remove disc and rinse in 20 µl of miliQ water using gentle pipetting, use 20 µl in PCR Process B Paper functionalised with 20 µl SiQAC (3-TPAC) solution, dried for 30' and washed in 5 mM TRIS-Cl [pH 9.0], 0.2 mM MgCl2 then dried and either;
  i. Apply the sample, dry for 20', remove disc and add 20 µl of miliQ water for PCR, or
  ii. Apply the sample, dry for 20', remove disc and rinse in 20 µl of miliQ water using gentle pipetting, use 20 µl in PCR Process C Paper functionalised with 20 µl SiQAC (3-TPAC) and dried for 30' and either;
  i. Apply the sample, dry for 20', remove disc and rinse in 20 µl of miliQ water using gentle pipetting, use 20 µl in PCR, or
  ii. Apply the sample, dry for 20', remove disc and add 20 µl of 5 mM TRIS-Cl [pH 9.0], 0.2 mM MgCl2 for PCR; or
  iii. Apply the sample, dry for 20', remove disc and rinse in 20 µl of 5 mM TRIS-Cl [pH 9.0], 0.2 mM MgCl2 using gentle pipetting, use 20 µl in PCR An alternative composite sample paper is shown in FIG. 4. The sample paper includes a first layer of cellulose fibres, and a second layer of nitrocellulose fibres. It may also include a support layer.

A sample (for example, sputum) to be assayed is spotted onto the sample paper. The paper may incorporate a reagent which changes colour when a sample has been applied; for example, the reagent may change colour when wet. The first cellulose layer acts as an absorbent layer, and captures cellular content, and provides vertical and horizontal fluid flow. The second nitrocellulose layer provides rapid removal of water via lateral flow, and improves drying speed of a sample applied to the paper; drying is further enhanced by the air gap separating the paper from the base portion when the cartridge is being used. This operation allows a sample to be dried and prepared for further assay within a few minutes. The paper may also be impregnated with reagents to lyse cells and release nucleic acids, if desired; for example it may be functionalised as described above. Alternatively, or in addition, the paper may include one or more reagents for conducting a desired reaction, for example, the paper may include lyophilised enzymes and nucleotides for use in a PCR reaction.

The invention claimed is:

1. A sample preparation cartridge comprising:
  a lower portion having a base and a raised portion projecting from the base;
  at least one sprung member projecting from the base of the lower portion;
  an upper portion engageable with and removable from the lower portion, and comprising at least one well shaped opening; wherein
  the at least one sprung member is located between the lower and upper portions when the upper portion is engaged with the lower portion;
  the at least one sprung member projects from the lower portion further than the raised portion;
  and wherein the raised portion is configured to align with the well shaped opening,
  the cartridge being configured such that a sample preparation paper placed between the upper and lower portions located adjacent the well shaped opening rests on the at least one sprung member so as to separate the paper from the lower portion; and
  wherein when a user applies pressure to the upper portion the at least one sprung member compresses, and thereby urges the paper into contact with the raised portion of the lower portion.

2. The cartridge of claim 1 comprising two sprung members.

3. The cartridge of claim 1 wherein the at least one sprung member is formed integrally with the lower portion.

4. The cartridge of claim 1 wherein the upper portion is made from a plastics material.

5. The cartridge of claim 1 wherein the upper portion is translucent and/or clear.

6. The cartridge of claim 4 wherein the plastics material is hydrophobic.

7. The cartridge of claim 1 further comprising a sample preparation paper located between the upper and lower portions.

8. The cartridge of claim 7 wherein the sample preparation paper is a composite paper.

9. The cartridge of claim 7 or 8 wherein the sample preparation paper is functionalised with one or more biocidal agents capable of i) weakening cell membrane, cell wall, viral envelope, or viral capsid of biological material in a sample; or ii) lysing cellular or viral material in a sample.

10. The cartridge of claim 9 wherein the biocidal agent comprises multiple functional groups, including a binding moiety; a hydrophobic moiety; and a charged moiety.

11. The cartridge of claim 10 wherein the hydrophobic moiety is an alkyl chain.

12. The cartridge of claim 10 wherein the charged moiety is positively charged.

13. The cartridge of claim 10 wherein the binding moiety comprises a hydroxyl group.

14. The cartridge of claim 9 wherein the biocidal agent is a silylated quaternary ammonium compound (SiQAC).

15. A kit comprising:
a) a sample preparation cartridge comprising:
a lower portion having a base and a raised portion projecting from the base;
at least one sprung member projecting from the base of the lower portion;
an upper portion engageable with and removable from the lower portion, and comprising at least one well shaped opening; wherein
the at least one sprung member is located between the lower and upper portions when the upper portion is engaged with the lower portion;
the at least one sprung member projects from the base of the lower portion further than the raised portion,
and wherein the raised portion is configured to align with the well shaped opening;
the cartridge being configured such that a sample preparation paper placed between the upper and lower portions located adjacent the well shaped opening rests on the at least one sprung member so as to separate the paper from the base of the lower portion;
wherein when a user applies pressure to the upper portion the at least one sprung member compresses, and thereby urges the paper into contact the raised portion of the lower portion; and
b) a sample preparation paper.

16. The kit of claim 15, wherein the sample preparation paper is a composite paper.

17. The cartridge of claim 1 comprising four sprung members.

18. The cartridge of claim 4 wherein the plastics material is modified with groups to assist in lysis of cellular material in samples.

19. The cartridge of claim 18 wherein the plastics material is functionalised with a silylated quaternary ammonium compound (SiQAC).

20. The cartridge of claim 19 wherein the plastics material is functionalised with 3-(trimethoxysilyl) propyldimethyloctadecyl ammonium chloride (3-TPAC).

21. The cartridge of claim 8 wherein the paper is a composite cellulose paper comprising a lateral flow layer.

22. The cartridge of claim 11 wherein the hydrophobic moiety is C5-C30 alkyl.

23. The cartridge of claim 11 wherein the hydrophobic moiety is C10-C20 alkyl.

24. The cartridge of claim 12 wherein the charged moiety is a quaternary ammonium group.

25. The cartridge of claim 14 wherein the biocidal agent is 3-(trimethoxysilyl) propyldimethyloctadecyl ammonium chloride (3-TPAC).

* * * * *